(12) United States Patent
Ernst et al.

(10) Patent No.: US 7,271,296 B2
(45) Date of Patent: Sep. 18, 2007

(54) METHOD FOR THE PRODUCTION OF PHYTOFLUENE

(75) Inventors: Hansgeorg Ernst, Speyer (DE); Klaus Henrich, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/595,503

(22) PCT Filed: Oct. 15, 2004

(86) PCT No.: PCT/EP2004/011582

§ 371 (c)(1),
(2), (4) Date: Apr. 24, 2006

(87) PCT Pub. No.: WO2005/042446

PCT Pub. Date: May 12, 2005

(65) Prior Publication Data

US 2007/0004925 A1      Jan. 4, 2007

(30) Foreign Application Priority Data

Oct. 24, 2003   (DE)  ................. 103 49 983

(51) Int. Cl.
C07C 45/72    (2006.01)
C07C 43/303   (2006.01)
C07C 2/00     (2006.01)
C07D 319/06   (2006.01)

(52) U.S. Cl. .................. 568/460; 568/596; 549/369; 585/600

(58) Field of Classification Search ............... None
See application file for complete search history.

(56) References Cited

U.S. PATENT DOCUMENTS

| 4,482,582 A | 11/1984 | Weisman |
| 4,757,096 A | 7/1988 | Berthevas et al. |
| 4,810,729 A | 3/1989 | Davis et al. |
| 6,063,825 A | 5/2000 | Isobe et al. |
| 2003/0032689 A1 | 2/2003 | Lutter et al. |

FOREIGN PATENT DOCUMENTS

| EP | 0 269 346 | 6/1988 |
| EP | 0 312 920 | 4/1989 |

(Continued)

OTHER PUBLICATIONS

Lambertin, F. et al., "New Retinoid Analogs from .delta. Pyronene, a Natural Synthon"., Eur. J. Org. Chem. 1999, pp. 1489-1494.

(Continued)

*Primary Examiner*—Sikarl A. Witherspoon
(74) *Attorney, Agent, or Firm*—Connolly Bove Lodge and Hutz

(57) ABSTRACT

The invention relates to a process for preparing phytofluene of the formula I,

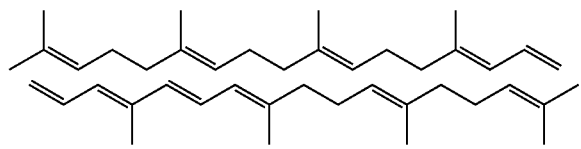

where
a) a phosphonium salt of the formula II is condensed with an aldehyde of the formula III

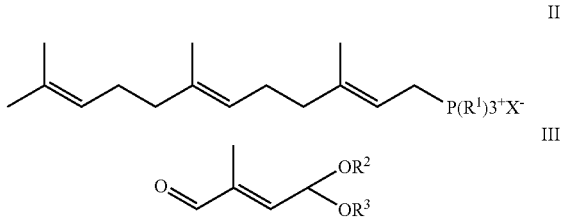

in a Wittig reaction to give an acetal of the formula IV

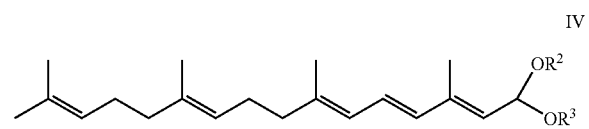

b) the condensation product of the formula IV is subjected to an acid-catalyzed acetal hydrolysis to give the aldehyde of the formula V

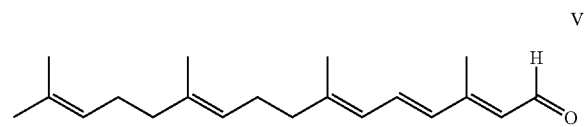

c) and V is condensed in a further Wittig reaction with a phosphonium salt of the formula VI to give phytofluene

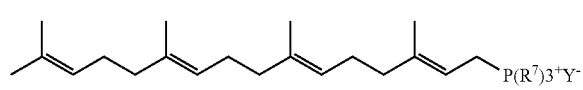

where the radicals $R^1$, $R^2$ and $R^7$, and $X^-$ and $Y^-$ have the meaning sated in the description.

8 Claims, No Drawings

FOREIGN PATENT DOCUMENTS

| | | |
|---|---|---|
| EP | 0 897 940 | 2/1999 |
| EP | 1 247 827 | 10/2002 |
| WO | 00/13654 | 3/2000 |
| WO | WO-00/13654 | 3/2000 |
| WO | 03/041678 | 5/2003 |
| WO | WO-03/041678 | 5/2003 |

OTHER PUBLICATIONS

Davis, J. B. et al., "Carotenoids and Related Compounds. Part XV. The Structure and Synthesis of Phytoene, Phytofluene, ξ-Carotene, and Neurosporene". J Chem. Soc. (C), 1966, pp. 2154-2165.

Bienayme, H., Yezeguelian, C., "Palladium-Catalysed Vinylation of tertiary Allylic Alcohols: a New Protocol for the Synthesis of Isoprenoid Aldehydes". Tetrahedron, vol. 50. No. 11, 1994, pp. 3389-3396.

Davis, J.B. et al., "The Structures of Phytoene, Phytofluene, ξ-Carotene, and Neurosporene". Proc. Chem. Soc. 1961, p. 261.

Pattenden, G. et al., "Carotenoids and Related Compounds. Part XVIII. Synthesis of *cis*- and Di-*cis*- Polyenes by Reactions of the Wittig Type." J. Chem. Soc. (C), 1968, pp. 1984 ff.

Bestmann, H.J. et al., "Synthese von modifizierten Retinalen". Liebigs Ann. Chem., 1986, pp. 479-98.

Lambertin, F. et al., "New Retinoid Analogs from .delta. Pyronene, a Natural Synthon"., Eur. J. Org. Chem. 1999, pp. 1489-1494.

Davis, J. B. et al., "Carotenoids and Related Compounds. Part XV. The Structure and Synthesis of Phytoene, Phytofluene, ζ-Carotene, and Neurosporene". J Chem. Soc. (C), 1966, pp. 2154-2165.

Bienayme, H., Yezeguelian, C., "Palladium-Catalysed Vinylation of tertiary Allylic Alcohols: a New Protocol for the Synthesis of Isoprenoid Aldehydes". Tetrahedron, vol. 50. No. 11, 1994, pp. 3389-3396.

Davis, J.B. et al., "The Structures of Phytoene, Phytofluene, ζ-Carotene, and Neurosporene". Proc. Chem. Soc. 1961, p. 261.

Pattenden, G. et al., "Carotenoids and Related Compunds, Part XVII. Synthesis of cis- and Di-cis-Polyenes by Reactions of the Wittig Type." J. Chem. Soc. (C), 1968, pp. 1984 ff.

METHOD FOR THE PRODUCTION OF PHYTOFLUENE

CROSS REFERENCE TO RELATED APPLICATIONS

This application is a National Stage entry under 35 U.S.C. §371 of PCT/EP2004/011582 filed on Oct. 15, 2004. International application PCT/EP2004/011582 claims priority to German application 10349983.1 filed on Oct. 24, 2003, the entire of contents of each of the above applications are incorporated by reference herein.

The present invention relates to a novel process for preparing phytofluene (7,8,11,12,7',8'-hexahydrolycopene) of the formula I.

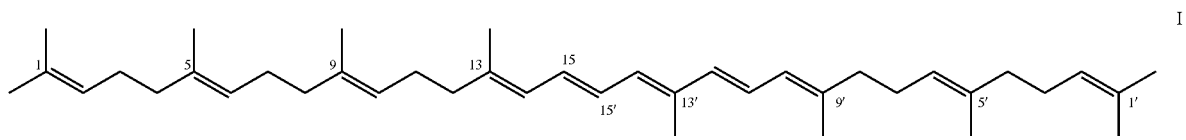

Phytofluene is an agent which is in demand for protecting the skin from damage induced by oxygen or UV radiation (described inter alia in WO 03/041678 and WO 00/13654).

Phytofluene, a precursor in the biogenesis of the carotenoid lycopene, can in fact be isolated from natural sources. However, the availability of these sources is limited and, since phytofluene is accompanied by other biogenetic precursors such as, for example, phytoene or zeta-carotene, it is moreover difficult to obtain the pure agent by this route.

The strategy of choice is therefore total chemical synthesis. The synthetic challenge with phytofluene is that its molecular structure is nonsymmetrical (the $C_{11}$—$C_{12}$ bond is saturated; the $C_{11}$—$C_{12}$ bond is olefinic).

A prior art process for preparing phytofluene is as follows (J. Chem. Soc. C., 1966, 2154 f.; Proc. Chem. Soc. 1961, 261):

The industrially available nerolidol VII is converted in two stages into the aldehyde VIII. The $C_{11}'$=$C_{12}'$ double bond is then introduced by a Wittig-Horner reaction of VIII with the phosphonate IX. This is followed by reduction of the ester X to the alcohol XI and reoxidation thereof with manganese dioxide to the aldehyde V.

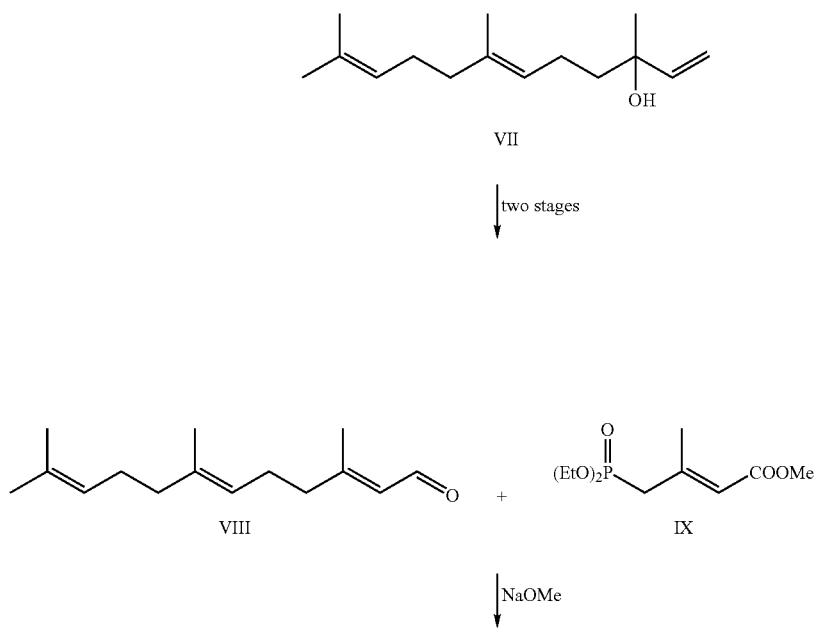

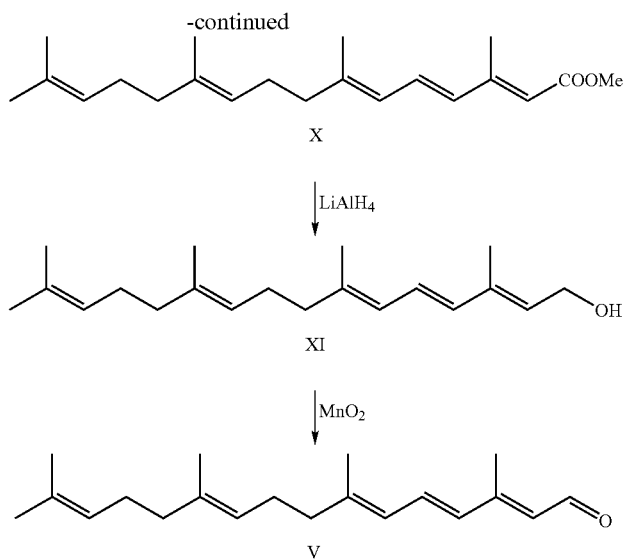

In the last stage, V undergoes Wittig condensation with the phosphonium salt VI, which is obtainable from geranyllinalool, to give phytofluene.

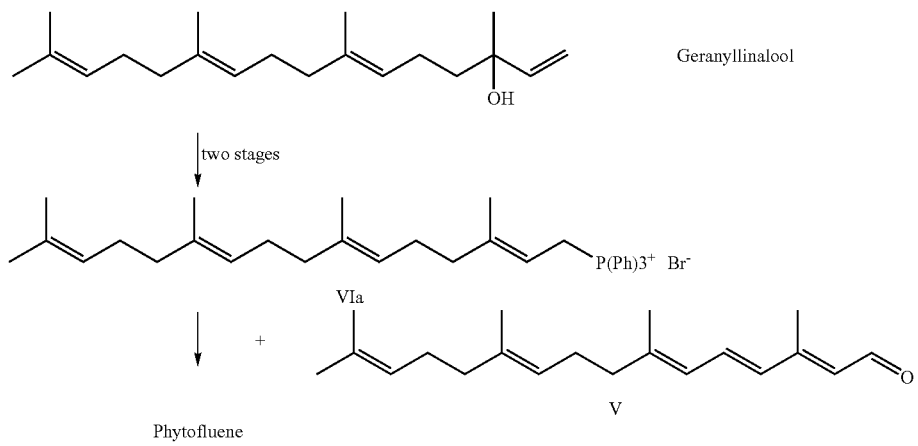

The crucial disadvantage of this synthesis is that the conversion of VII into the aldehyde V is extremely time-consuming and involves many stages. The alanate reduction (X→XI) and manganese dioxide oxidation (XI→V) stages involve costly and—in the case of LiAlH$_4$—dangerous handling of solids. In addition, the phosphonate IX is not industrially available and must be prepared in two further stages from β-methylcrotonic ester (J. Chem. Soc. C., 1968, 1984 f.). Because of these disadvantages, this synthesis does not represent an industrially and economically interesting route to phytofluene.

It was therefore the object of the present invention to provide a process for preparing phytofluene which does not have the prior art disadvantages mentioned above.

This object has been achieved by a process for preparing phytofluene of the formula I,

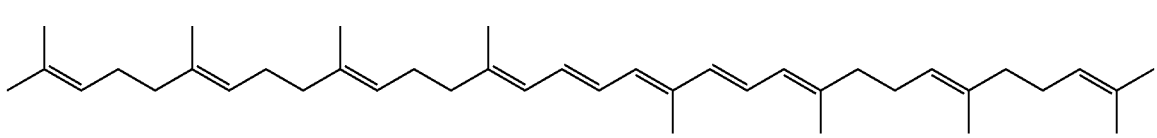

which comprises
a) condensing a phosphonium salt of the formula II

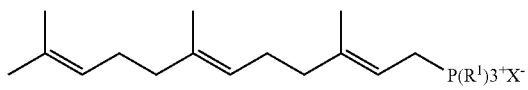

in which $R^1$ is aryl and $X^-$ is the anion equivalent of an inorganic or organic acid, with an aldehyde of the formula III

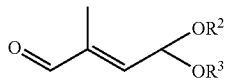

in a Wittig reaction to give an acetal of the formula IV

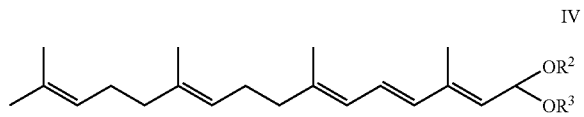

where the substituents $R^2$ and $R^3$ are independently of one another $C_1$—$C_8$-alkyl, or together with the oxygen atom and the carbon atom to which they are bonded may form a 1,3-dioxolane or 1,3-dioxane ring of the following structures

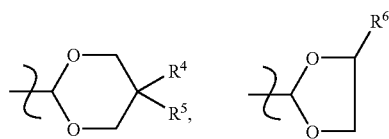

in which $R^4$ and $R^5$, and $R^6$ may each independently of one another be hydrogen or $C_1$—$C_4$-alkyl,
b) subjecting the condensation product of the formula IV to an acid-catalyzed acetal hydrolysis to give the aldehyde of the formula V

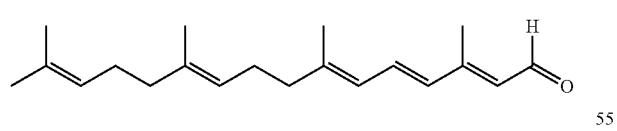

c) and condensing V in a further Wittig reaction with a phosphonium salt of the formula VI,

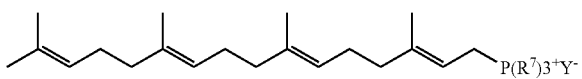

in which $R^7$ is aryl and $Y^-$ is the anion equivalent of an inorganic or organic acid, in give phytofluene.

In the case of open-chain acetals, alkyl radicals which may be mentioned for $R^2$ and $R^3$ are linear or branched $C_1$—$C_8$-alkyl chains, e.g. methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1 2-trimethylpropyl, 1,2,2-trimethylpropyl, 1-ethyl-1-methylpropyl, 1-ethyl-2-methylpropyl, n-heptyl and n-octyl.

Preferred alkyl radicals for $R^2$ and $R^3$ are methyl, ethyl, n-propyl and 1-methylethyl, particularly preferably methyl and ethyl.

Alkyl radicals which may be mentioned for $R^4$ to $R^5$ are linear or branched $C_1$—$C_4$-alkyl chains, e.g. methyl, ethyl, n-propyl, 1-methylethyl, n-butyl, 1-methylpropyl, 2-methylpropyl and 1,1-dimethylethyl.

Preferred radicals for $R^4$ to $R^5$ are hydrogen and methyl.

The term aryl for $R^1$ and $R^7$ refers to customary aryl radicals occurring in phosphonium salts, such as phenyl, toluene, naphthyl, optionally substituted in each case, preferably phenyl.

The radicals $X^-$ and $Y^-$ are each an anion equivalent of an inorganic or organic acid, preferably of a strong inorganic or organic acid.

The term strong acid comprises hydrohalic acids (especially hydrochloric acid and hydrobromic acid), sulfuric acid, phosphoric acid, sulfonic acids and other inorganic or organic acids having a comparable degree of dissociation. Strong organic acids also mean in this connection $C_1$—$C_6$-alkanoic acids such as formic acid, acetic acid, propionic acid, butyric acid, and caproic acid.

Particularly preferred anions which should be mentioned are those of acids selected from the group consisting of hydrochloric acid, hydrobromic acid, sulfuric acid, phosphoric acid, formic acid, acetic acid and sulfonic acids. Very particularly preferably $Cl^-$, $Br^-$, $C_nH_{2n+1}$—$SO_3^-$ (with n=1-4), $Ph$—$SO_3^-$, $p$-$Tol$-$SO_3^-$ or $CF_3$—$SO_3^-$.

The first step a) of the process of the invention comprises the olefination reaction of a phosphonium salt of the general formula II with a $C_5$-acetal aldehyde of the general formula III

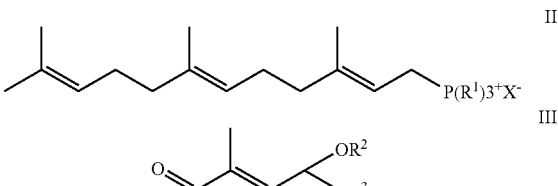

in which the substituents have the meaning given above.

Nerolidol VII is used as starting compound and can be converted in a manner known per se (J. Chem. Soc C., 1966, 2154 f.) into the phosphonium salt of the formula II. This process is described for $X^-$=bromide, but $X^-$ may also be the anion of other strong acids such as, for example, chloride, hydrogen sulfate or sulfonate.

The Wittig condensation of the phosphonium salt II with the aldehyde III to give a $C_{20}$ acetal of the formula IV is carried out under the conditions typical of these reactions (see Carotenoids, Vol. 2, "Synthesis", p. 79 ff.; Birkhäuser Verlag, 1996, and literature cited therein).

The condensation of II with III can be carried out for example in an inert organic solvent, e.g. in open-chain or cyclic ethers such as diethyl ether, diisopropyl ether, methyl tert-butyl ether 1,4-dioxane or THF, in halogenated hydrocarbons such as dichloromethane, chloroform, in aromatic hydrocarbons such as toluene, xylene or benzene or in polar solvents such as dimethylformamide, dimethyl sulfoxide or acetonitrile. Preferred solvents are diethyl ether, toluene, THF and DMSO or mixtures thereof.

It is possible to use as base at bases customary for such condensations, e.g. alkali metal hydroxides such as sodium hydroxide, potassium hydroxide or lithium hydroxide, alkali metal hydrides such as sodium hydride or potassium hydride.

Suitable bases are additionally lithium organyls such as, for example, n-butyllithium, tert-butyllithium, phenyllithium or alkali metal amides such as lithium, potassium or sodium amide, lithium diisopropylamide or else alkali meal hexamethyldisilazides. The base preferably employed for the Wittig reaction of the invention is sodium or potassium hexamethyldisilazide, n-butyllithium and potassium or sodium amide.

The amount of base employed is ordinarily in the range from 0.8 to 5 mol, preferably 1 to 3 mol per mole of the phosphonium salt II employed.

If X⁻ is a halide anion, it is also possible advantageously to employ oxiranes as latent bases (see Chem. Ber. 1974, 107, 2050).

The bases preferably use for these Wittig reactions are lithium organyls in hexane or solutions of alkali metal alcoholates in the corresponding alcohol or oxiranes, especially 1,2-epoxybutane, without additional solvent or mixed with one of the abovementioned solvents or with a lower alkanol.

A preferred embodiment of process step a) comprises using as phosphonium salt the bromide of the formula IIa

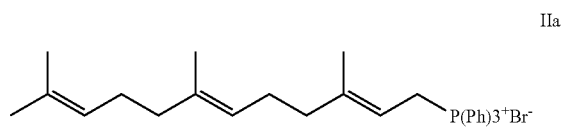

IIa and as aldehyde a compound of the formula IIIa

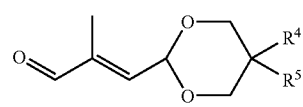

IIIa in which the substituents $R^4$ and $R^5$ are independently of one another hydrogen and/for methyl, preferably in each case jointly hydrogen or methyl, particularly preferably jointly methyl.

The phosphonium salt II can be prepared in a manner known per se from nerolidol VII (J. Chem. Soc. C., 1966, 2154 f.). This process is described for X⁻=bromide, but X⁻ may also be the anion of other strong acids such as, for example, chloride, hydrogen sulfate or sulfonate.

Aldehydes of type III are known as building blocks for industrial polyene syntheses ("Carotenoids", Vol. 2., "Synthesis", p. 125 f. Birkhäuser Verlag, 1996, and literature cited therein).

In step b) of the process of the invention, the acetal group in IV or IVa is hydrolyzed to the aldehyde function V.

All conditions known to the skilled worker for, preferably, acid-catalyzed acetal cleavage are suitable in principle here, e.g. using dilute mineral acids such as sulfuric acid. It has proved to be particularly suitable to catalyze the hydrolysis of the acetal function with citric acid. The citric acid is expediently employed in an amount of from 5 to 50 mol %, preferably 20 to 30 mol %, based on the compound of the formula IV or IVa. The hydrolysis preferably takes place in aqueous media, especially in a mixture of water with a water-miscible organic solvent such as $C_1$—$C_4$ alkanols, e.g. methanol, ethanol or isopropanol, preferably ethanol at a temperature of, suitably, from 0° C. to the boiling point of the solvent, preferably 25° C. to 55° C.

In the last step of the process, the aldehyde V obtained in this way is reacted in a manner known per se (J. Chem. Soc. C., 1966, 2154 f.) with the phosphonium salt VI to give phytofluene. This reaction takes place under conditions typical of a Wittig reaction, concerning which reference is made to the details mentioned at the outset.

The phosphonium salt VI which is preferably used is geranylgeranyltriphenyl-phosphonium bromide of the formula VIa

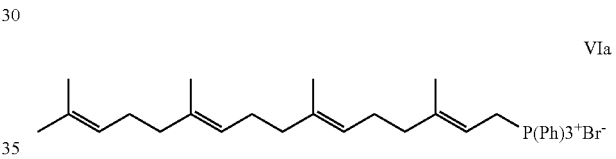

VIa

The invention also relates to a process for preparing the $C_{20}$ aldehyde of the formula V,

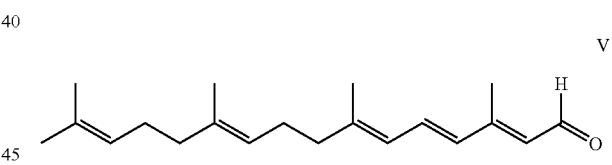

V which comprises a) condensing a phosphonium salt of the formula II

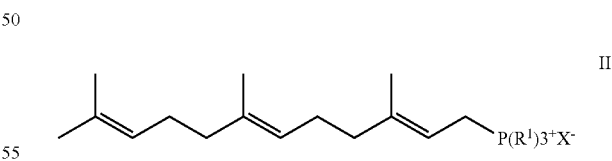

II in which Ris aryl and X⁻ is the anion equivalent of an inorganic or organic acid, with an aldehyde of the formula III

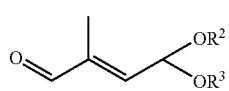

III in a Wittig reaction to give an acetal of the formula IV

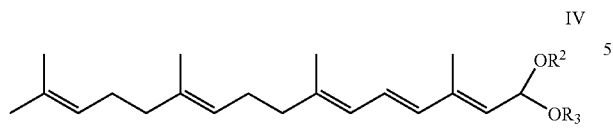

where the substituents $R^2$ and $R^3$ are independently of one other $C_1$—$C_8$-alkyl, or may form together with the oxygen atoms and the carbon atom to which they are bonded a 1,3-dioxolane or 1,3-dioxane ring of the following structures

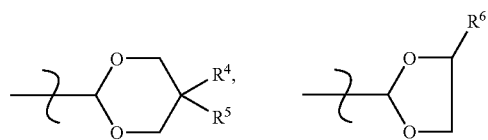

in which $R^4$ and $R^5$, and $R^6$ may each independently of one another be hydrogen or $C_1$—$C_4$-alkyl, b) subjecting the condensation product of the formula IV to an add-catalyzed acetal hydrolysis to give the aldehyde of the formula V.

Details of process steps a) and b) are to be found in the statements already made at the outset.

The invention additionally relates to acetals of the general formula IV,

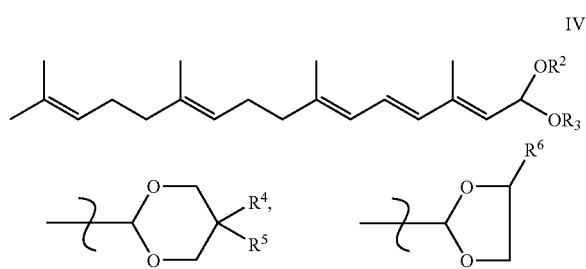

in which the substituents $R^2$ and $R^3$ are independently of one another $C_1$—$C_8$-alkyl, or may form together with the oxygen atoms and the carbon atom to which they are bonded a 1,3-dioxolane or 1,3-dioxane ring of the following structures in which $R^4$ and $R^5$, and $R^6$ may each independently of one another be hydrogen or $C_1$—$C_4$-alkyl.

For a more detailed description of the substituents $R^2$ to $R^6$, reference may be made to the statements made at the outset.

The acetal of the formula IVa is preferred

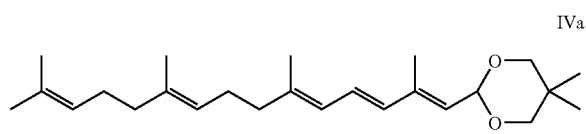

The process of the invention is explained in more detail by means of the following examples.

EXAMPLE 1 a. Preparation of the Acetal IVa 30.12 g (55 mmol) of farnesyltriphenylphosphonium bromide IIa ($X^-$=bromide) were suspended in 1000 ml of diethyl ether. At 0° C. to +5° C., 31.0 g of a 15% strength solution of n-butyllithium in hexane (=66.5 mmol of butyllithium) were run in over the course of 30 min. The resulting dark red solution was stirred at 0° C. to +5° C. for 30 min and then, at this temperature, a solution of 9.43 g (51 mmol) of aldehyde IIa ($R^4$ and $R^5$=methyl) in 100 ml of diethyl ether was added dropwise.

After stirring at 0° C. to +50° C. for one hour, 200 ml of ice-water were added dropwise. The upper organic phase was separated off, washed twice with 200 ml of ice-water each time, dried over sodium sulfate and concentrated in a rotary evaporator. The crude product was purified by flash filtration on silica gel (eluent: cyclohexane/methyl tert-butyl ether 4/1). 19.0 g of acetal IVa were obtained as a viscous yellowish oil which was employed in this form directly in the acetal cleavage.

b. Preparation of the Aldehyde V 19.0 g of acetal IVa from example 1a) were dissolved in 200 ml of ethanol. Then a solution of 2.9 g (13.7 mmol) of citric acid in 48 ml of water was added, and the mixture was heated under reflux for 1 hour. The reaction mixture was diluted with 550 ml of hexane and 220 ml of ethyl acetate and washed twice with 40 ml of saturated sodium bicarbonate solution each time and once with 40 ml of saturated brine. The combined aqueous phases were re-extracted twice with 80 ml each time of a 1/1 hexane/ethyl acetate mixture.

The two organic phases were combined, washed with 40 ml of saturated brine and dried together with the first organic phase over sodium sulfate. The solvent was distilled off in a rotary evaporator at 50° C. down to 20 mbar.

The residue from evaporation was purified by flash chromatography on silica gel (eluent: cyclohexane/ethyl acetate=20/1). 13.4 g of aldehyde V were obtained. This corresponded to a yield of 92% of theory based on the aldehyde IIIa employed, c. Preparation of Phytofluene 26.2 g (42.5 mmol) of geranylgeranyltriphenylphosphonium bromide VI (X–=bromide) were suspended in 770 ml of diethyl ether. At 0° C. to +5° C., 21.7 g of a 15% strength solution of n-butyllithium in n-hexane (=50.8 mmol of butyllithium) were run in. The resulting dark red solution was stirred at 0° C. to +5° C. for 30 min. Then a solution of 11.1 g (38.8 mmol) of aldehyde V was added dropwise over the course of 30 min, and the mixture was stirred 0° C. to +5° C. for 1 hour. The mixture was then hydrolyzed by dropwise addition of 150 ml of ice-water. The upper organic phase was separated off, washed twice with 150 ml of ice-water each time, dried over sodium sulfate and evaporated in a rotary evaporator at 50° C. down to 20 mbar.

The crude product was purified by flash chromatography on silica gel (eluent: cyclohexane). 14.9 g of phytofluene (E/Z isomer mixture) were obtained as a yellow oil. Yield: 70.7% of theory.

We claim:

1. A process for preparing phytofluene of the formula I,

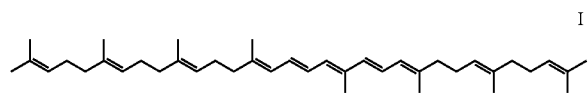

which comprises a) condensing a phosphonium salt of the formula II,

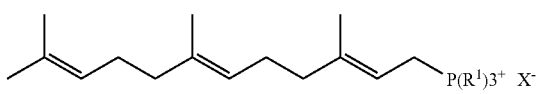

in which $R^1$ is aryl and $X^-$ is the anion equivalent of an inorganic or organic acid, with an aldehyde of the formula III

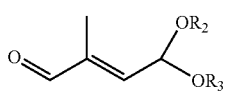

in a Wittig reaction to give an acetal of the formula IV

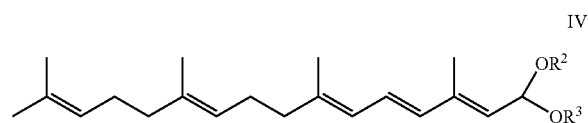

where the substituents $R^2$ and $R^3$ are independently of one another $C_1$—$C_8$-alkyl, or together with the oxygen atom and the carbon atom to which they are bonded may form a 1,3-dioxolane or 1,3-dioxane ring of the following structures

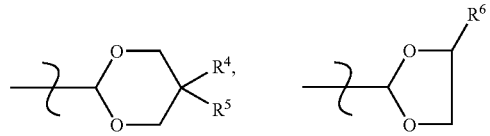

in which $R^4$ and $R^5$, and $R^6$ may each independently of one another be hydrogen or $C_1$—$C_4$-alkyl, b) subjecting the condensation product of the formula IV to an acid-catalyzed acetal hydrolysis to give the aldehyde of the formula V

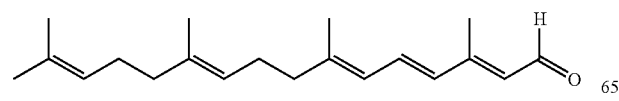

c) and condensing V in a further Wittig reaction with a phosphonium salt of the formula VI,

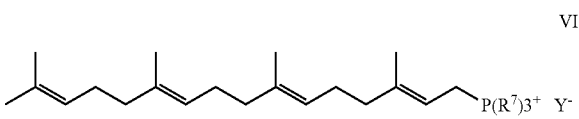

in which $R^7$ is aryl and $Y^-$ is the anion equivalent of an inorganic or organic acid, to give phytofluene.

2. The process according to claim 1, wherein in step a) the phosphonium salt of the formula II is reacted with the aldehyde of the formula IIIa to give the acetal of the formula IVa

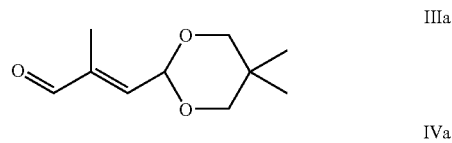

3. The process according to claim 1, wherein $X^-$ and $Y^-$ of the phosphonium salts II and VI are independently of one another the anion equivalent of an acid selected from the group consisting of hydrohalic acid, sulfuric acid, phosphoric acid, formic acid, acetic acid and sulfonic acid.

4. The process according to claim 3, wherein $X^-$ and $Y^-$ are $Cl^-$, $Br^-$, $C_nH_{2n+1}$—$SO_3^-$ with n=1-4, Ph—$SO_3^-$, p-Tol—$SO_3^-$ or $CF_3$—$SO_3^-$.

5. The process according to claim 1, wherein the hydrolysis of the acetal IV in step b) is carried out in the presence of citric acid as acidic catalyst.

6. A process for preparing the $C_{20}$ aldehyde of the formula V,

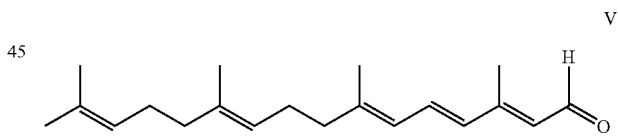

which comprises a) condensing a phosphonium salt of the formula II,

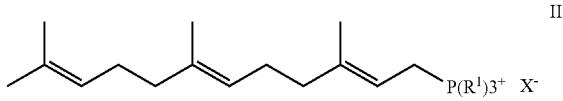

in which $R^1$ is aryl and $X^-$ is the anion equivalent of an inorganic or organic acid, with an aldehyde of the formula III

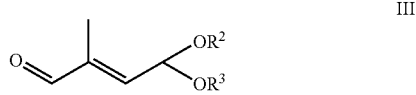

in a Wittig reaction to give an acetal of the formula IV

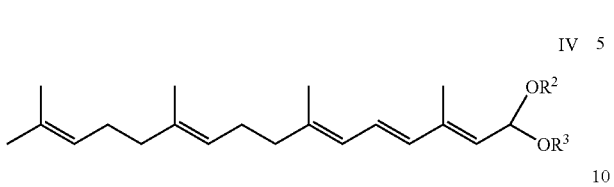

where the substituents $R^2$ and $R^3$ are independently of one another $C_1$—$C_8$-alkyl, or may form together with the oxygen atoms and the carbon atom to which they are bonded a 1,3-dioxolane or 1,3-dioxane ring of the following structures

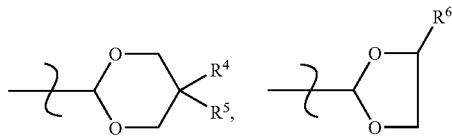

in which $R^4$ and $R^5$, and $R^6$ may each independently of one another be hydrogen or $C_1$—$C_4$-alkyl, b) subjecting the condensation product of the formula IV to an acid-catalyzed acetal hydrolysis to give the aldehyde of the formula V.

7. An acetal of the general formula IV

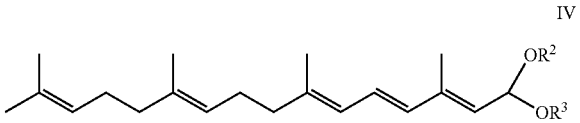

in which the substituents $R^2$ and $R^3$ are independently of one another $C_1$—$C_8$-alkyl or may form together with the oxygen atoms and the carbon atom to which they are bonded a 1,3-dioxolane or 1,3-dioxane ring of the following structures

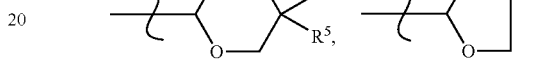

in which $R^4$ and $R^5$, and $R^6$ may each independently of one another be hydrogen or $C_1$—$C_4$-alkyl.

8. The acetal of the formula IVa

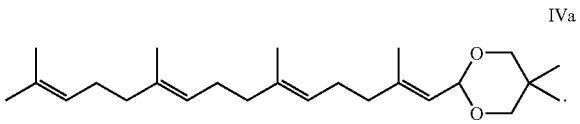

\* \* \* \* \*